(12) United States Patent
Tetsuka (10) Patent No.: US 11,453,649 B2
(45) Date of Patent: Sep. 27, 2022

(54) GRAPHENE NANOSTRUCTURE

(71) Applicant: KABUSHIKI KAISHA TOYOTA CHUO KENKYUSHO, Nagakute (JP)

(72) Inventor: Hiroyuki Tetsuka, Nagakute (JP)

(73) Assignee: KABUSHIKI KAISHA TOYOTA CHUO KENKYUSHO, Nagakute (JP)

( * ) Notice: Subject to any disclaimer, the term of this patent is extended or adjusted under 35 U.S.C. 154(b) by 408 days.

(21) Appl. No.: 16/634,638

(22) PCT Filed: Jul. 17, 2018

(86) PCT No.: PCT/JP2018/026677
§ 371 (c)(1),
(2) Date: Jan. 28, 2020

(87) PCT Pub. No.: WO2019/026604
PCT Pub. Date: Feb. 7, 2019

(65) Prior Publication Data
US 2021/0061774 A1    Mar. 4, 2021

(30) Foreign Application Priority Data

Aug. 1, 2017   (JP) ............................. JP2017-149449

(51) Int. Cl.
*C07D 241/12*   (2006.01)
*C01B 32/194*   (2017.01)
(Continued)

(52) U.S. Cl.
CPC .......... *C07D 241/12* (2013.01); *C01B 32/194* (2017.08); *C07D 401/04* (2013.01);
(Continued)

(58) Field of Classification Search
CPC .. C07D 241/12; C07D 401/04; C07D 403/04; C01B 32/194; C01B 2204/22;
(Continued)

(56) References Cited

U.S. PATENT DOCUMENTS

2016/0005894 A1*  1/2016  Zhang .................. H01L 31/028
                                                                257/29
2017/0047592 A1*  2/2017  Surendranath ........ C07F 15/006

FOREIGN PATENT DOCUMENTS

CN      106582766 A   *  4/2017  ............. H01M 4/00
JP      2017-092210 A    5/2017
WO      WO-2009101449 A2 *  8/2009  ............. B82Y 10/00

OTHER PUBLICATIONS

Du "Synthesis and characterization of amphiphilic graphene." Science China, 47(2), pp. 244-248. (Year: 2014).*
(Continued)

*Primary Examiner* — Tri V Nguyen
(74) *Attorney, Agent, or Firm* — Oliff PLC (57) ABSTRACT

A graphene nanostructure has a nanographene, a π conjugated functional group bonded to the nanographene via a pyrazine skeleton, and at least one Br group and/or at least one CN group introduced into the π conjugated functional group. A graphene nanostructure preferably has an average size of 1 nm or larger to 100 nm or smaller, a band gap of 0.01 eV or higher to 1.2 eV or lower, and/or a HOMO level of −6.0 eV or higher to −4.0 eV or lower. As the π conjugated functional group into which the Br group(s) and/or the CN group(s) are/is introduced, a 4-bromobenzene group, a 4,5-dibromobenzene group, a 5-bromopyridine group, a 5-bromopyrazine group, a benzonitrile group, a phthalonitrile group, or a 2,3-dicyanopyrazine group is desirable.

7 Claims, 3 Drawing Sheets

(51) Int. Cl.
  *C07D 401/04* (2006.01)
  *C07D 403/04* (2006.01)
  *H01L 51/00* (2006.01)
  *H01L 51/42* (2006.01)
  *B82Y 15/00* (2011.01)
  *B82Y 40/00* (2011.01)

(52) U.S. Cl.
  CPC ........ *C07D 403/04* (2013.01); *H01L 51/0045* (2013.01); *H01L 51/428* (2013.01); *B82Y 15/00* (2013.01); *B82Y 40/00* (2013.01); *C01B 2204/22* (2013.01); *C01B 2204/32* (2013.01)

(58) Field of Classification Search
  CPC ............. C01B 2204/32; H01L 51/0045; H01L 51/428; H01L 31/10; B82Y 30/00; B82Y 40/00; B01J 27/24; B01J 31/1805; B01J 31/0244
  USPC .......................... 252/500, 510, 511; 544/357
  See application file for complete search history.

(56) References Cited

OTHER PUBLICATIONS

Tetsuka et al.; "Graphene/nitrogen-functionalized graphene quantum dot hybrid broadband photodetectors with a buffer layer of boron nitride nanosheets;" Nanoscale; 2016; pp. 19677-19683; vol. 8.

Zhang et al.; "Solution-Processed Graphene Quantum Dot Deep-UV Photodetectors;" ACS Nano; 2015; pp. 1561-1570; vol. 9, No. 2.

Sep. 11, 2018 Search Report issued in International Patent Application No. PCT/JP2018/026677.

Feb. 4, 2020 International Preliminary Report on Patentability issued in International Patent Application No. PCT/JP2018/026677.

* cited by examiner

GRAPHENE NANOSTRUCTURE

FIELD OF THE INVENTION

The present invention relates to a graphene nanostructure, more specifically, a graphene nanostructure that can detect light from deep ultraviolet to infrared with a wavelength of 1,000 nm or more and can be used as a broadband optical sensor.

BACKGROUND OF THE INVENTION

A graphene is a sheet material comprising one atomic layer to several atomic layers of a graphite crystal, and has the characteristics of an extremely high carrier mobility at room temperature and being able to absorb light of all wavelengths from deep ultraviolet to terahertz. An attempt therefore is being made to create a broadband optical sensor responsive to light from deep ultraviolet to infrared by using such unique properties of a graphene. A problem, however, is that a graphene has metallic properties and the sensitivity of an optical sensor using the graphene is low.

Meanwhile, when a graphene is refined to a size of several nanometers, a graphene nanostructure converted into a semiconductor, such as a graphene quantum dot, can be obtained. Further, an attempt is being made to improve the sensitivity of an optical sensor by using such a graphene nanostructure.

For example, Patent Literature 1 discloses an optical sensor having a field effect transistor whose channel comprises a graphene (graphene FET), and a light absorption layer that is formed on the surface of the channel and comprises a nitrogen functionalized nanographene.

The literature describes that, when a graphene FET and a nitrogen functionalized nanographene are combined, an optical sensor that has a high photoconductive gain, does not contain a harmful element, and responds in the region from ultraviolet to near infrared is obtained.

Further, Non-patent Literature 1 discloses an optical sensor that uses a graphene nanostructure having a band gap of 1.57 eV as a light absorption layer and responds to light with a wavelength of 250 nm to 940 nm.

Furthermore, Non-patent Literature 2 discloses an optical sensor that uses a graphene nanostructure having a band gap of 3.8 eV as a light absorption layer and responds to deep ultraviolet (wavelength of 300 nm or less).

The size of a graphene nanostructure is correlated with a band gap. In general, as the size of a graphene nanostructure increases, a band gap reduces and even light of a long wavelength can be absorbed. Only by optimizing the size of a graphene nanostructure, however, sensitivity (absorbance) cannot be improved in a wide wavelength range.

On the other hand, as disclosed in the Patent Literature 1, when a nitrogen functional group is introduced into a graphene nanostructure, light of 440 to 785 nm can be absorbed. By this method, however, sensitivity is insufficient in an infrared region with a wavelength of 1,000 nm or more.

CITATION LIST

Patent Literature

[Patent Literature 1] Japanese Unexamined Patent Application Publication 2017-092210

Non-Patent Literature

[Non-patent Literature 1] Tetsuka, H., Nagoya, A. & Tamura, S. Graphene/nitrogen-functionalized graphene quantum dot hybrid broadband photodetectors with a buffer of boron nitride nanosheets, Nanoscale 8, 19677-19683 (2016)

[Non-patent Literature 2] Zhang, Q., Jie, J., Diao, S., Shao, Z., Zhang, Q., Wang, L., Deng, W., Hu, W., Xia, H., Yuan, X. & Lee, S.-T. Solution-Processed Graphene Quantum Dot Deep-UV Photodetectors. ACS Nano 9, 1561-1570 (2015)

SUMMARY OF THE INVENTION

A problem to be solved by the present invention is to provide a graphene nanostructure that can detect light from deep ultraviolet to infrared with a wavelength of 1,000 nm or more.

Further, another problem to be solved by the present invention is to provide a graphene nanostructure that can be used as a broadband optical sensor.

In order to solve the above problems, a graphene nanostructure according to the present invention is characterized by having:

a nanographene;

a π conjugated functional group bonded to the nanographene via a pyrazine skeleton; and at least one Br group and/or at least one CN group introduced into the π conjugated functional group.

A nanographene has semiconductivity (band gap $E_g>0$ eV) and can absorb light. The nanographene, however, has low light sensitivity over the entire wavelength range and particularly has almost no sensitivity in the infrared region with a wavelength of 1,000 nm or more.

On the other hand, when a π conjugated functional group is introduced into a nanographene via a pyrazine skeleton, light sensitivity in a short wavelength range improves. In addition to this, when a Br group and/or a CN group are/is introduced into the π conjugated functional group, light sensitivity in a short wavelength range further improves as well as a light absorption edge is shifted toward a longer wavelength of 1,000 nm or more, and light sensitivity in a long wavelength range improves significantly.

This is thought to be due to the concerto effect of:

(a) expansion of π conjugateness of a nanographene by bonding a π conjugated functional group to the nanographene via a pyrazine skeleton; and (b) a push-pull effect between a Br group and/or a CN group and a π electron cloud of the nanographene by binding the Br group and/or the CN group of a strong electron-attracting property to the π conjugated functional group.

DETAILED DESCRIPTION OF THE PREFERRED EMBODIMENT

An embodiment according to the present invention is explained hereunder in detail.

[1. Graphene Nanostructure]

Figure 1:
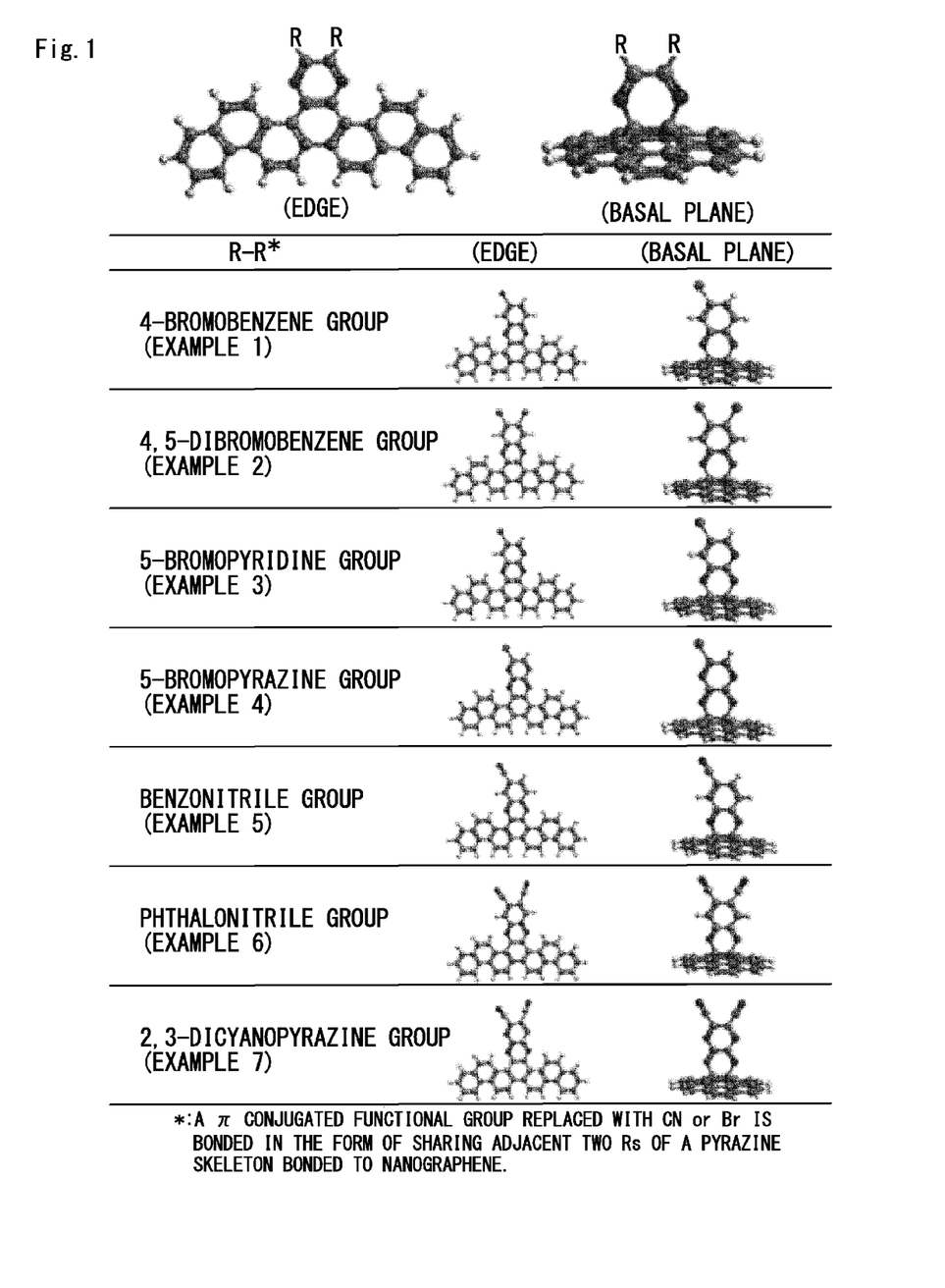
FIG. 1 is schematic views of graphene nanostructures according to the present invention.

FIG. 1 shows schematic views of graphene nanostructures according to the present invention. In FIG. 1, a graphene nanostructure according to the present invention has:

a nanographene;

a π conjugated functional group bonded to the nanographene via a pyrazine skeleton; and at least one Br group and/or at least one CN group introduced into the π conjugated functional group.

[1.1. Nanographene]

A "Nanographene" means a substance that: is a material having a two-dimensional sheet-like structure comprising a carbon ring structure and an $sp^2$ bonded aromatic ring; and shows semiconductivity (Eg>0 eV) in the state of introducing a π conjugated functional group and a Br group and/or a CN group. A nanographene may comprise a single-layer sheet or a multilayer sheet. In general, when a nanographene shows semiconductivity, a graphene nanostructure in which a π conjugated functional group and a Br group and/or a CN group are introduced into the nanographene also shows semiconductivity.

[1.2. π Conjugated Functional Group and Pyrazine Skeleton]

A "π conjugated functional group" means a functional group derived from an unsaturated cyclic compound having a structure in which atoms having π electrons are arranged annularly. As an atom having a π electron for example, there are C, N, and the like. The π conjugated functional group is bonded to a nanographene via a pyrazine skeleton.

A "pyrazine skeleton" means a pyrazine ring ($=C_4N_2=$) bonded to an edge and/or a basal plane of a nanographene with only one side shared. Either "2nd and 3rd carbons" or "5th and 6th carbons" in the pyrazine ring are shared between the nanographene and the pyrazine skeleton, and the other carbons are shared between the pyrazine skeleton and a π conjugated functional group.

The upper row in FIG. 1 shows a schematic view representing a state of bonding a pyrazine skeleton to an edge or a basal plane of a nanographene. A pyrazine skeleton is bonded to a π conjugated functional group replaced with a Br group or a CN group in the form of sharing adjacent two Rs located at a tip of the pyrazine skeleton.

As an unsaturated cyclic compound that is a base of a π conjugated functional group for example, there are:

(a) an unsaturated cyclic compound having an annular structure comprising only C (for example, benzene ($C_6H_6$), azulene ($C_{10}H_8$), cyclobutadiene ($C_4H_4$), etc.);

(b) an unsaturated cyclic compound having an annular structure comprising C and N (for example, pyridine ($C_5H_5N$), pyrazine ($C_4H_4N_2$), phenazine ($C_{12}H_8N_2$), pyridazine ($C_4H_4N_2$), pyrimidine ($C_4H_4N_2$), etc.);

(c) an unsaturated cyclic compound having an annular structure comprising C and O (for example, furan ($C_4H_4O$), etc.);

(d) an unsaturated cyclic compound having an annular structure comprising C and N and including an N—H bond (for example, pyrrole ($C_4H_5N$), pyrazole ($C_3H_4N_2$), imidazole ($C_3H_4N_2$), etc.); and (e) annulene with more than 6 carbon atoms (for example, cyclooctatetraene ($C_8H_8$), cyclotetradecaheptaene ($C_{14}H_{14}$), cyclooctadecanonaene ($C_{18}H_{18}$), etc.).

A graphene nanostructure may be a substance including either any one or two or more of those π conjugated functional groups.

[1.3. Br Group, CN Group]

A Br group and/or a CN group are/is introduced into a π conjugated functional group. "A Br group and/or a CN group are/is introduced" means that hydrogen atoms/a hydrogen atom bonded to atoms/an atom constituting an annular structure of a π conjugated functional group are/is replaced with a Br group and/or a CN group. Either one or both of the Br group and the CN group may be introduced into the π conjugated functional group.

Further, either a Br group or a CN group or two or more of Br groups and/or CN groups may be introduced into a π conjugated functional group. Since both the Br group and the CN group have a strong electron-attracting property, as the number of the Br groups and the CN groups introduced into a π conjugated functional group increases, a push-pull effect of a nanographene with a π electron increases and a light absorption wavelength becomes longer. Even if the Br group or the CN group is introduced excessively, however, there is no difference in effect and no profit. The numbers of the Br groups and the CN groups therefore may desirably be selected optimally in accordance with a purpose.

As a π conjugated functional group in which a Br group and/or a CN group are/is introduced for example, there are a 4-bromobenzene group ($C_6H_3Br=$), a 4,5-dibromobenzene group ($C_6H_2Br_2=$), a 5-bromopyridine group ($C_5H_2BrN=$), a 5-bromopyrazine group ($C_4HBrN_2=$), a benzonitrile group ($C_6H_3CN=$), a phthalonitrile group ($C_6H_2(CN)_2=$), a 2,3-dicyanopyrazine group ($C_4N_2(CN)_2=$), etc. (refer to FIG. 1).

[1.4. Average Size]

A "size of a graphene nanostructure" means the maximum length of a sheet when the sheet is viewed from a normal direction.

An "average size" means the average value of the sizes of n (n≥5) pieces of graphene nanostructures selected randomly.

An average size of graphene nanostructures influences a band gap Eg. When an average size of graphene nanostructures is too small, Eg increases excessively and semiconductivity may sometimes be lost. An average size therefore is desirably 1 nm or larger. An average size is more desirably 3 nm or larger.

On the other hand, when an average size of graphene nanostructures is too large, semiconductivity is lost. An average size therefore is desirably 100 nm or smaller. An average size is more desirably 50 nm or smaller and yet more desirably 30 nm or smaller.

[1.5. Average Thickness]

An "average thickness of graphene nanostructures" means the average value of the thicknesses of n (n≥5) pieces of graphene nanostructures selected randomly.

As a method for measuring a thickness for example, there are:

(a) a method of directly measuring the thickness of a sheet with an atomic force microscope (AFM);

(b) a method of obtaining a thickness from the number of layers of a graphene nanostructure observed with a transmission electron microscope (TEM) in consideration of an ideal thickness for one layer (0.34 nm); etc.

By any of the methods, a nearly identical result is obtained.

An average thickness of graphene nanostructures influences semiconductivity and permeability of solar ray. When a graphene nanostructure is too thick, semiconductivity may sometimes be lost. An average thickness of graphene nanostructures therefore is desirably 100 nm or smaller. An average thickness is more desirably 50 nm or smaller and yet more desirably 10 nm or smaller.

[1.6. Band Gap]

When a graphene nanostructure according to the present invention is applied to an optical sensor, the graphene nanostructure has to be a substance that can create an electron-hole pair by absorbing light. To that end, the graphene nanostructure has to be a substance that shows semiconductivity (Eg>0 eV).

Whether or not a graphene nanostructure shows semiconductivity and the magnitude of a band gap (Eg) depends mainly on the average size (or average mass) of the graphene nanostructure and the number of Br groups and/or CN groups.

In general, as Eg of a graphene nanostructure reduces, the graphene nanostructure can absorb longer wavelength light. When Eg is too small, however, a carrier can be thermally excited and the graphene nanostructure cannot be used as a broadband optical sensor. Eg therefore is desirably 0.01 eV or higher.

On the other hand, when Eg is excessively large, light of a long wavelength cannot be absorbed. Eg therefore is desirably 1.2 eV or lower. Eg is more desirably 1.0 eV or lower and yet more desirably 0.8 eV or lower.

[1.7. HOMO Level]

A graphene nanostructure according to the present invention can be used for various applications, and, in particular, is preferably used as a material of a light absorption layer of a phototransistor using a graphene in a channel.

In general, a photoexcited carrier has a short lifetime and tends to disappear by recombination. In contrast, when a light absorption layer having a long photoexcited carrier lifetime is combined with a graphene field effect transistor (graphene FET), one (for example, an electron) of a carrier excited in the light absorption layer moves rapidly toward a graphene layer but the other (for example, a hole) of the carrier remaining in the light absorption layer has a long lifetime. As a result, the photoconductive gain of an optical sensor improves.

In general, as a LUMO (Lowest Unoccupied Molecular Orbital) level difference or a HOMO (Highest Occupied Molecular Orbital) level difference between a light absorption layer and a graphene reduces, one of a carrier tends to move toward a graphene layer. In order to obtain a high photoconductive gain, the LUMO level difference or the HOMO level difference between the two materials has to be 2 eV or lower. A LUMO level difference or a HOMO level difference is desirably 1 eV or lower.

A LUMO level difference or a HOMO level difference between a graphene nanostructure according to the present invention and a graphene used for a channel of a graphene FET depends mainly on the type of a π conjugated functional group and the number of Br groups and/or CN groups, those being introduced into the graphene nanostructure.

The HOMO level of a graphene is about −4.6 eV. Meanwhile, when the type of a π conjugated functional group and the number of Br groups and/or CN groups are optimized, the HOMO level of a graphene nanostructure becomes −6.0 eV or higher to −4.0 eV or lower. When a graphene nanostructure having such a HOMO level is combined with a graphene FET therefore, an electron can move rapidly toward a graphene layer and a photoconductive gain improves.

[1.8. Application]

A graphene nanostructure according to the present invention has a wide light absorption wavelength range and hence is suitable particularly as a material used for a broadband optical sensor. More specifically, the applications are:

(a) a material of a light absorption layer used for a graphene phototransistor;

(b) a material of a channel and a light absorption layer used for a phototransistor;

(c) a material of a channel layer used for a photodiode;

(d) a material of a channel and a light absorption layer used for an image sensor; etc.

[2. Manufacturing Method of Graphene Nanostructure]

A manufacturing method of a graphene nanostructure according to the present invention includes:

a dispersion process of obtaining a dispersion liquid by dispersing a nanographene in an aqueous solution in which a diamine compound containing a π conjugated functional group replaced with a Br group and/or a CN group is dissolved; and a heating process of heating the dispersion liquid to 100° C. or higher.

[2.1. Dispersion Process]

Firstly, a dispersion liquid is obtained by dispersing a nanographene in an aqueous solution in which a diamine compound containing a π conjugated functional group replaced with a Br group and/or a CN group is dissolved (dispersion process).

[2.1.1. Diamine Compound]

A "diamine compound containing a π conjugated functional group replaced with a Br group and/or a CN group (hereunder referred to merely as "diamine compound")" means a substance that: is a chemical compound in which primary amine groups are bonded to adjacent two positions of a π conjugated functional group replaced with a Br group and/or a CN group respectively; and can dissolve or disperse in water.

As such a diamine compound for example, there are 4-bromo-1,2-diaminobenzene $(C_6H_3Br(NH_2)_2)$, 4,5-dibromo-1,2-phenylenediamine $(C_6H_2Br_2 (NH_2)_2)$, 2,3-diamino-5-bromopyridine $(C_5HNBr(NH_2)_2)$, 2,3-diamino-5-bromopyrazine $(C_4HN_2Br(NH_2)_2)$, 3,4-diaminobenzonitrile $(C_6H_3CN(NH_2)_2)$, 4,5-diaminophthalonitrile $(C_6H_2(CN)_2 (NH_2)_2)$, 5,6-diamino-2,3-dicyanopyrazine $(C_6N_2(CN)_2 (NH_2)_2)$, etc.

As a starting material, any one or two or more of the diamine compounds may be used.

A diamine compound is used in the state of an aqueous solution in which the diamine compound is dissolved or dispersed in water. The concentration of a diamine compound contained in the aqueous solution is not particularly limited, and an optimum concentration may be selected in accordance with a type of a starting material, a required characteristic, and the like. The concentration of a diamine compound is usually 0.1 to 10 mg/mL.

[2.1.2. Nanographene]

A nanographene can be synthesized by:

(a) dispersing a graphite oxide or a graphene oxide in an alkaline aqueous solution and heating them to 60° C. or higher in a sealed container; or (b) oxidizing nanographite particles by using an oxidant (potassium permanganate, potassium nitrate, or the like) in a strong acid (concentrated sulfuric acid) for example.

Here, a "graphite oxide" means a substance in which an oxygen-containing functional group (for example, a —COOH group, an —OH group, a —C—O—C— group, or the like) is bonded to an edge and/or a basal plane of a graphene layer constituting a graphite. The graphite oxide is obtained by oxidizing a graphite by using an oxidant (potassium permanganate, potassium nitrate, or the like) in a strong acid (concentrated sulfuric acid) for example.

A "graphene oxide" means a sheet material obtained by exfoliating a graphite oxide between layers. The graphene oxide can be obtained by dispersing a graphite oxide in an aqueous solution and applying ultrasonic waves.

In the present invention, as a starting material, either one or both of a graphite oxide before exfoliation and a graphene oxide after exfoliation may be used.

[2.1.3. Dispersion Liquid]

A nanographene is added to an aqueous solution containing a diamine compound. The quantity of a nanographene contained in a dispersion liquid is not particularly limited, and an optimum quantity may be selected in accordance with a type of a starting material, a required characteristic, and the like. The quantity of a nanographene is usually 0.1 to 50 mg/mL.

[2.2. Heating Process]

Successively, a nanographene is dispersed in an aqueous solution in which a diamine compound is dissolved or dispersed, and then the dispersion liquid is heated (heating process).

The heating is applied for increasing a reaction speed. When a heating temperature exceeds the boiling point of a dispersion liquid, the heating is applied in a sealed container.

When a heating temperature is too low, the reaction does not progress sufficiently in a realistic time. A heating temperature therefore has to be 100° C. or higher. A heating temperature is more desirably 120° C. or higher and yet more desirably 140° C. or higher.

On the other hand, when a heating temperature is too high, a Br group or a CN group, those being replaced or bonded, or a primary amine group may possibly fall off. Further, an expensive pressure vessel is required and a manufacturing cost increases. A heating temperature therefore is desirably 260° C. or lower. A heating temperature is more desirably 240° C. or lower and yet more desirably 220° C. or lower.

As a heating time, an optimum time is selected in accordance with a heating temperature. In general, as a heating temperature rises, the reaction can proceed in a short period of time. A heating time is usually 1 to 20 hours.

An obtained graphene nanostructure may be used for various applications as it is. Otherwise, washing, filtration, and/or dialysis may be applied if necessary.

[3. Effect]

A nanographene has semiconductivity (band gap Eg>0 eV) and can absorb light. The nanographene, however, has low light sensitivity over the entire wavelength range and particularly has almost no sensitivity in an infrared region with a wavelength of 1,000 nm or more. On the other hand, when the size of a nanographene is increased, a light absorption edge can be shifted to a longer wavelength to some extent (about 600 to 700 nm). Only by optimizing the size of a nanographene, however, a light absorption edge cannot be shifted to 1,000 nm or more.

On the contrary, when a π conjugated functional group is introduced into a nanographene via a pyrazine skeleton, light sensitivity in a short wavelength range improves. In addition to that, when a Br group and/or a CN group are/is introduced into the π conjugated functional group, the light sensitivity in a short wavelength range improves further as well as a light absorption edge is shifted to a longer wavelength of 1,000 nm or more, and the light sensitivity in a long wavelength range improves significantly.

A nanographene has an electron-donating property and an N atom has the function of enhancing the electron-donating property of the nanographene. When a π conjugated functional group is bonded to a nanographene via a pyrazine skeleton therefore, the π conjugateness of the nanographene expands.

Meanwhile, both a Br group and a CN group have a strong electron-attracting property, respectively. When a Br group and/or a CN group of a strong electron-attracting property are/is bonded to a π conjugated functional group therefore, a push-pull effect is generated between the Br group and/or the CN group and a π electron cloud of the nanographene and a π orbit expands.

It is estimated that a light absorption wavelength is shifted to a longer wavelength of 1,000 nm or more by the concerto effect of the expansion of the π conjugateness of a nanographene and the push-pull effect.

When a graphene nanostructure according to the present invention is used, a broadband optical sensor that can detect light from deep ultraviolet to infrared with a wavelength of 1,000 nm or more and has a light absorption edge in a wavelength of 1,000 nm or more can be manufactured.

EXAMPLES

Examples 1 to 7 and Comparative Examples 1 to 2

[1. Preparation of Dispersion Liquid]

1.1. Example 1: 4-bromobenzene Functionalized Graphene Nanostructure Dispersion Liquid 1 mg of a nanographene was dispersed in an aqueous solution of 5 mL in which 1 mg of a diamine compound was dispersed. As the diamine compound, a 4-bromo-1,2-diaminobenzene was used.

The obtained dispersion liquid was heated at 180° C. for 10 hours in a sealed container. After the heating, washing was applied sufficiently and a 4-bromobenzene functionalized graphene nanostructure was separated. The obtained graphene nanostructure was dispersed in a dimethylformamide solvent and a 4-bromobenzene functionalized graphene nanostructure dispersion liquid was obtained.

1.2. Example 2: 4,5-dibromobenzene Functionalized Graphene Nanostructure Dispersion Liquid A 4,5-dibromobenzene functionalized graphene nanostructure dispersion liquid was prepared similarly to Example 1 except that a 4,5-dibromo-1,2-phenylenediamine was used as a diamine compound.

1.3. Example 3: 5-bromopyridine Functionalized Graphene Nanostructure Dispersion Liquid A 5-bromopyridine functionalized graphene nanostructure dispersion liquid was prepared similarly to Example 1 except that a 2,3-diamino-5-bromopyridine was used as a diamine compound.

1.4. Example 4: 5-bromopyrazine Functionalized Graphene Nanostructure Dispersion Liquid A 5-bromopyrazine functionalized graphene nanostructure dispersion liquid was prepared similarly to Example 1 except that a 2,3-diamino-5-bromopyrazine was used as a diamine compound.

1.5. Example 5: Benzonitrile Functionalized Graphene Nanostructure Dispersion Liquid A benzonitrile functionalized graphene nanostructure dispersion liquid was prepared similarly to Example 1 except that a 3,4-diaminobenzonitrile was used as a diamine compound.

1.6. Example 6: Phthalonitrile Functionalized Graphene Nanostructure Dispersion Liquid A phthalonitrile functionalized graphene nanostructure dispersion liquid was prepared similarly to Example 1 except that a 4,5-diaminophthalonitrile was used as a diamine compound.

1.7. Example 7: 2,3-dicyanopyrazine Functionalized Graphene Nanostructure Dispersion Liquid A 2,3-dicyanopyrazine functionalized graphene nanostructure dispersion liquid was prepared similarly to Example 1 except that a 5,6-diamino-2,3-dicyanopyrazine was used as a diamine compound.

1.8. Comparative Example 1: Benzene Functionalized Graphene Nanostructure Dispersion Liquid A benzene functionalized graphene nanostructure dispersion liquid was prepared similarly to Example 1 except that a 1,2-phenylenediamine was used as a diamine compound.

1.9. Comparative Example 2: Nanographene Dispersion Liquid

A nanographene dispersion liquid was obtained by dispersing a nanographene as it was in a dimethylformamide solvent.

[2. Test Method]
[2.1. Morphological Observation]

An average size of graphene nanostructures was measured with a transmission electron microscope (2,000 EX, made by JEOL Ltd.).

[2.2. Absorption Spectrum, Band Gap]

An absorption spectrum and a band gap of a graphene nanostructure were measured with a UV-VIS-NIR spectrophotometer (UV-3600 and ISR-3100, made by Shimadzu Corporation).

[2.3. Homo Level]

A HOMO level of a graphene nanostructure was measured with a photoelectron spectrometer (AC-2, made by RIKEN KEIKI Co., Ltd.).

[3. Results]
[3.1. Morphological Observation]

Figure 2:
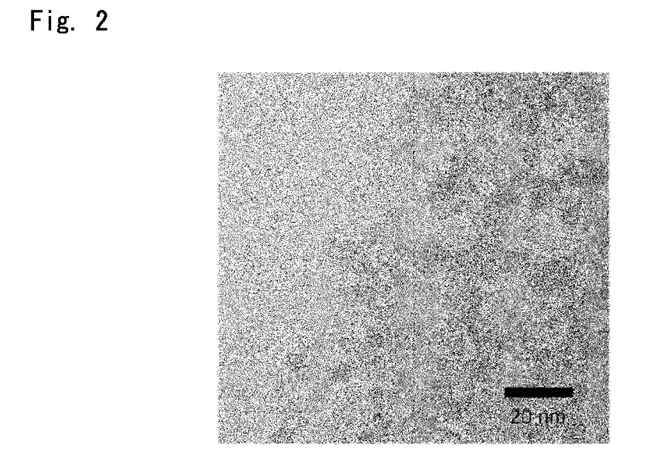
FIG. 2 is a transmission electron micrograph of a graphene nanostructure (Example 1)

FIG. 2 shows a transmission electron micrograph of the 4-bromobenzene functionalized graphene nanostructure (Example 1). From FIG. 2, it is obvious that the average sizes of the graphene nanostructures are 3 to 15 nm.

[3.2. Absorption Spectrum]

Figure 3:
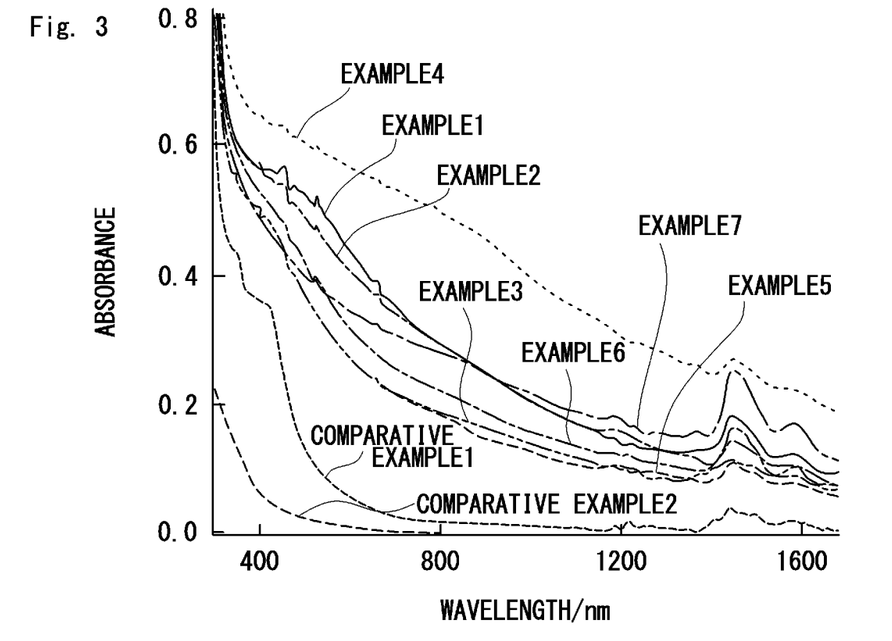
FIG. 3 is absorption spectra of graphene nanostructures (Examples 1 to 7 and Comparative Example 1) and a nanographene (Comparative Example 2)

FIG. 3 shows absorption spectra of the graphene nanostructures (Examples 1 to 7 and Comparative Example 1) and the nanographene (Comparative Example 2). FIG. 3 shows the following:

(1) the nanographene (Comparative Example 2) has low absorbances over the entire wavelength range;

(2) the benzene functionalized graphene nanostructure (Comparative Example 1) has greatly improved absorbances in the short wavelength range in comparison with Comparative Example 2. Comparative Example 1, however, hardly shows absorbance at a wavelength of 1,000 nm or more; and (3) it is confirmed that each of Examples 1 to 7 has a large absorbance at a wavelength of 1,000 nm or more.

From these, it has been clarified that it is necessary to introduce a π conjugated functional group into a nanographene via a pyrazine skeleton and introduce a Br group and/or a CN group into the π conjugated functional group in order to improve the light absorption of the nanographene at a longer wavelength of 1,000 nm or more.

[3.3. Band Gap and HOMO Level]

Table 1 shows the band gaps and the HOMO levels of the graphene nanostructures obtained in Examples 1 to 7 and Comparative Example 1. Table 1 shows the following:

(1) the band gap and the HOMO level of Comparative Example 1 are 1.57 eV and −5.58 eV, respectively; and (2) each of Examples 1 to 7 shows a HOMO level equivalent to Comparative Example 1. In contrast, each of Examples 1 to 7 has a lower band gap than Comparative Example 1. Further, it is recognized that the absorbance tends to improve as the band gap reduces (refer to FIG. 3).

TABLE 1

|  | BAND GAP (eV) | HOMO LEVEL (eV) |
| --- | --- | --- |
| COMPARATIVE EXAMPLE 1 | 1.57 | −5.58 |
| EXAMPLE 1 | 0.60 | −5.55 |
| EXAMPLE 2 | 0.97 | −5.73 |
| EXAMPLE 3 | 1.15 | −5.63 |
| EXAMPLE 4 | 0.76 | −5.24 |
| EXAMPLE 5 | 1.03 | −5.61 |
| EXAMPLE 6 | 0.95 | −5.52 |
| EXAMPLE 7 | 0.87 | −5.42 |

[3.4. Relationship Between Average Size and Band Gap]

Figure 4:
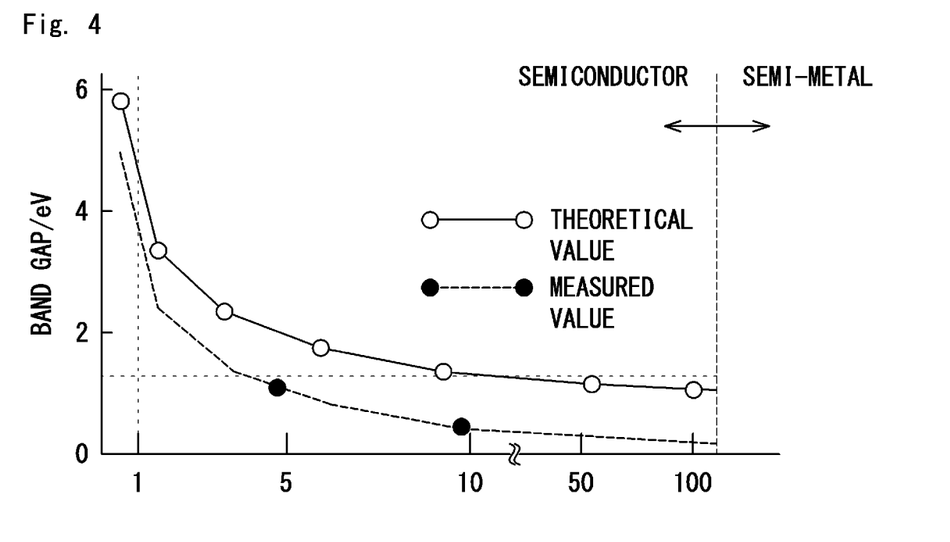
FIG. 4 is a graph showing a relationship between an average size and a band gap of a graphene nanostructure.

FIG. 4 shows a relationship between an average size and a band gap of a graphene nanostructure. Here, both the measured values and the theoretical values are shown in FIG. 4. FIG. 4 shows the following:

(1) as an average size increases, a band gap reduces. When an average size exceeds 100 nm, however, semiconductivity is lost;

(2) an average size of several nm or larger is desirable in order to reduce a band gap to 1.2 eV or lower; and (3) when an average size reduces to 1 nm or smaller, a band gap increases and semiconductivity is lost.

Although the embodiments according to the present invention have heretofore been explained in detail, the present invention is not limited to the above embodiments at all and can be modified variously within the range not departing from the tenor of the present invention.

A graphene nanostructure according to the present invention can be used for a material of a light absorption layer used for a broadband optical sensor and other applications.

What is claimed is:

1. A graphene nanostructure, comprising:
   a nanographene;
   a π conjugated functional group bonded to the nanographene via a pyrazine skeleton wherein the pyrazine skeleton is directly bonded to an edge and/or a basal plane of the nanographene; and
   at least one Br group and/or at least one CN group introduced into the π conjugated functional group,
   wherein the graphene nanostructure has an absorbance of at least 0.1 for light having a wavelength of 1,000 nm.

2. The graphene nanostructure according to claim 1, wherein an average size is 1 nm or larger to 100 nm or smaller.

3. The graphene nanostructure according to claim 1, wherein a band gap is 0.01 eV or higher to 1.2 eV or lower.

4. The graphene nanostructure according to claim 1, wherein a HOMO level is −6.0 eV or higher to −4.0 eV or lower.

5. The graphene nanostructure according to claim 1, wherein the π conjugated functional group into which the Br group(s) and/or the CN group(s) are/is introduced is at least a functional group selected from the group consisting of a 4-bromobenzene group, a 4,5-dibromobenzene group, a 5-bromopyridine group, a 5-bromopyrazine group, a benzonitrile group, a phthalonitrile group, and a 2,3-dicyanopyrazine group.

6. The graphene nanostructure according to claim 1, wherein a base of the r conjugated functional group is selected from the group consisting of (a) an unsaturated cyclic compound having an annular structure comprising only C, (b) an unsaturated cyclic compound having an annular structure comprising C and N, (c) an unsaturated cyclic compound having an annular structure comprising C and O, (d) an unsaturated cyclic compound having an annular structure comprising C and N and including an N—H bond, and (e) an annulene with more than 6 carbon atoms.

7. A broadband optical sensor comprising the graphene nanostructure according to claim 1.

\* \* \* \* \*